United States Patent
Kiyose et al.

(10) Patent No.: US 10,172,591 B2
(45) Date of Patent: Jan. 8, 2019

(54) ULTRASONIC DEVICE, ULTRASONIC PROBE, ULTRASONIC DIAGNOSTIC APPARATUS, AND METHOD OF MANUFACTURING ULTRASONIC DEVICE

(71) Applicant: SEIKO EPSON CORPORATION, Tokyo (JP)

(72) Inventors: Kanechika Kiyose, Nagano (JP); Toshikazu Uchiyama, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 1077 days.

(21) Appl. No.: 14/511,324

(22) Filed: Oct. 10, 2014

(65) Prior Publication Data

US 2015/0105663 A1    Apr. 16, 2015

(30) Foreign Application Priority Data

Oct. 11, 2013    (JP) .................................. 2013-213463

(51) Int. Cl.
*A61B 8/00* (2006.01)
*B06B 1/06* (2006.01)
(Continued)

(52) U.S. Cl.
CPC ............ *A61B 8/4494* (2013.01); *B06B 1/067* (2013.01); *B06B 1/0622* (2013.01); *A61B 8/14* (2013.01);
(Continued)

(58) Field of Classification Search
CPC ......... B06B 1/067; B06B 1/0622; B06B 1/06; A61B 8/4494; A61B 8/5207; A61B 8/461;
(Continued)

(56) References Cited

U.S. PATENT DOCUMENTS 5,434,827 A * 7/1995 Bolorforosh .......... B06B 1/0622
310/320
5,553,035 A * 9/1996 Seyed-Bolorforosh ......................
B06B 1/0622
310/320

(Continued)

FOREIGN PATENT DOCUMENTS

JP    61-217142 A    9/1986
JP    02-049640 A    2/1990
(Continued)

*Primary Examiner* — Michael Carey
*Assistant Examiner* — Don N Ho

(57) ABSTRACT

An ultrasonic device includes a substrate, a first piezoelectric body, a second piezoelectric body, and an acoustic matching section. The substrate has a first surface that is a flat surface. The first piezoelectric body is disposed on the first surface of the substrate. The second piezoelectric body is disposed on the first surface of the substrate. The second piezoelectric body has a different thickness from a thickness of the first piezoelectric body as measured from the first surface of the substrate. The acoustic matching section is disposed on the first piezoelectric body and the second piezoelectric body. The acoustic matching section has a first side facing the first piezoelectric body and the second piezoelectric body, and a second side opposite from the first side. A surface of the acoustic matching section on the second side is a flat surface parallel with the first surface of the substrate.

6 Claims, 10 Drawing Sheets

| k1 | k2 | d1 | t1 | d2 | t2 | $\frac{C_P}{C_S}$ | $C_S$ (m/s) WHEN $C_P$=4,000 (m/s) | APPLICABLE ACOUSTIC MATCHING MATERIALS | SUITABILITY OF ACOUSTIC MATCHING MATERIALS |
|---|---|---|---|---|---|---|---|---|---|
| | 3 | | | | $\frac{3C_S}{8f_1}$ | 0.5 | 8,000 | SPECIAL METALS | × |
| 1 | 5 | $\frac{C_P}{2f_1}$ | $\frac{C_S}{4f_1}$ | $\frac{C_P}{4f_1}$ | $\frac{5C_S}{8f_1}$ | 1.5 | 2,667 | POLYMER MATERIALS | ○ |
| | 7 | | | | $\frac{7C_S}{8f_1}$ | 2.5 | 1,600 | NATURAL RUBBERS | ◎ |
| | 9 | | | | $\frac{9C_S}{8f_1}$ | 3.5 | 1,143 | SILICON | ◎ |
| | : | : | : | : | : | : | : | : | : |
| 3 | 7 | $\frac{C_P}{2f_1}$ | $\frac{3C_S}{4f_1}$ | $\frac{C_P}{4f_1}$ | $\frac{7C_S}{8f_1}$ | 0.5 | 8,000 | SPECIAL METALS | × |
| | 9 | | | | $\frac{9C_S}{8f_1}$ | 1.5 | 2,667 | POLYMER MATERIALS | ○ |
| | : | : | : | : | : | : | : | : | : | n = 2

(51) Int. Cl.
*A61B 8/14* (2006.01)
*A61B 8/08* (2006.01)

(52) U.S. Cl.
CPC ............ *A61B 8/461* (2013.01); *A61B 8/5207* (2013.01); *Y10T 29/42* (2015.01)

(58) Field of Classification Search
CPC .... A61B 8/14; A61B 8/00; A61B 8/08; Y10T 29/42
USPC .......................................... 600/443; 310/334
See application file for complete search history.

(56) References Cited

U.S. PATENT DOCUMENTS

| | | | |
|---|---|---|---|
| 6,540,683 B1* | 4/2003 | Lin ....................... | B06B 1/0622 600/447 |
| 2002/0027400 A1* | 3/2002 | Toda ....................... | B06B 1/067 310/334 |
| 2007/0035204 A1* | 2/2007 | Angelsen ................. | B06B 1/064 310/311 |
| 2009/0260422 A1 | 10/2009 | Sugiura et al. | |
| 2013/0338507 A1 | 12/2013 | Onishi et al. | |

FOREIGN PATENT DOCUMENTS

| | | | |
|---|---|---|---|
| JP | 2002-336248 A | 11/2002 |
| JP | 2005-277988 A | 10/2005 |
| JP | 2009-0267510 A | 11/2009 |
| JP | 2009-296055 A | 12/2009 |
| JP | 2011-056103 A | 3/2011 |
| JP | 2013-255692 A | 12/2013 |

\* cited by examiner n = 2

| k1 | k2 | d1 | t1 | d2 | t2 | $\frac{C_P}{C_S}$ | $C_S$ (m/s) WHEN $C_P$=4,000 (m/s) | APPLICABLE ACOUSTIC MATCHING MATERIALS | SUITABILITY OF ACOUSTIC MATCHING MATERIALS |
|---|---|---|---|---|---|---|---|---|---|
| 1 | 3 | $\frac{C_P}{2f_1}$ | $\frac{C_S}{4f_1}$ | $\frac{C_P}{4f_1}$ | $\frac{3C_S}{8f_1}$ | 0.5 | 8,000 | Special Metals | × |
|  | 5 |  |  |  | $\frac{5C_S}{8f_1}$ | 1.5 | 2,667 | Polymer Materials | ○ |
|  | 7 |  |  |  | $\frac{7C_S}{8f_1}$ | 2.5 | 1,600 | Natural Rubbers | ◎ |
|  | 9 |  |  |  | $\frac{9C_S}{8f_1}$ | 3.5 | 1,143 | Silicon | ◎ |
|  | ⋮ |  |  |  | ⋮ | ⋮ | ⋮ | ⋮ | ⋮ |
| 3 | 7 | $\frac{C_P}{2f_1}$ | $\frac{3C_S}{4f_1}$ | $\frac{C_P}{4f_1}$ | $\frac{7C_S}{8f_1}$ | 0.5 | 8,000 | Special Metals | × |
|  | 9 |  |  |  | $\frac{9C_S}{8f_1}$ | 1.5 | 2,667 | Polymer Materials | ○ |
|  | ⋮ |  |  |  | ⋮ | ⋮ | ⋮ | ⋮ | ⋮ |

Fig. 4 n = 3

| k1 | k2 | d1 | t1 | d2 | t2 | $\frac{C_P}{C_S}$ | $C_S$ (m/s) WHEN $C_P$=4,000 (m/s) | APPLICABLE ACOUSTIC MATCHING MATERIALS | SUITABILITY OF ACOUSTIC MATCHING MATERIALS |
|---|---|---|---|---|---|---|---|---|---|
| 1 | 5 | $\frac{C_P}{2f_1}$ | $\frac{C_S}{4f_1}$ | $\frac{C_P}{6f_1}$ | $\frac{5C_S}{12f_1}$ | 0.5 | 8,000 | SPECIAL METALS | × |
|  | 7 |  |  |  | $\frac{7C_S}{12f_1}$ | 1.0 | 4,000 | CERAMICS | △ |
|  | 9 |  |  |  | $\frac{9C_S}{12f_1}$ | 1.5 | 2,667 | POLYMER MATERIALS | ○ |
|  | 11 |  |  |  | $\frac{11C_S}{12f_1}$ | 2.0 | 2,000 | POLYETHYLENE | ◎ |
|  | ⋮ |  |  |  | ⋮ | ⋮ | ⋮ | ⋮ | ⋮ |
| 3 | 11 | $\frac{C_P}{2f_1}$ | $\frac{3C_S}{4f_1}$ | $\frac{C_P}{6f_1}$ | $\frac{11C_S}{12f_1}$ | 0.5 | 8,000 | SPECIAL METALS | × |
|  | 13 |  |  |  | $\frac{13C_S}{12f_1}$ | 1.0 | 4,000 | CERAMICS | △ |
|  | 15 |  |  |  | $\frac{15C_S}{12f_1}$ | 1.5 | 2,667 | POLYMER MATERIALS | ○ |
|  | ⋮ |  |  |  | ⋮ | ⋮ | ⋮ | ⋮ | ⋮ |

Fig. 5

ULTRASONIC DEVICE, ULTRASONIC PROBE, ULTRASONIC DIAGNOSTIC APPARATUS, AND METHOD OF MANUFACTURING ULTRASONIC DEVICE

CROSS-REFERENCE TO RELATED APPLICATIONS

This application claims priority to Japanese Patent Application No. 2013-213463 filed on Oct. 11, 2013. The entire disclosure of Japanese Patent Application No. 2013-213463 is hereby incorporated herein by reference.

BACKGROUND

Technical Field

The present invention relates to an ultrasonic device, an ultrasonic probe, an ultrasonic diagnostic apparatus, and a method of manufacturing an ultrasonic device.

Related Art

Ultrasonic devices for transmitting and receiving ultrasonic waves have been widely used in ultrasonic diagnostic apparatuses and the like. Then, generally used in an ultrasonic device is a vibrator where electrodes are formed at both ends of a piezoelectric body of, inter alia, a piezoelectric ceramic, of which lead (Pb) zirconium titanate (PZT) is representative. Japanese Laid-Open Patent Publication No. 1-12-49640 discloses such an ultrasonic device. According thereto, ultrasonic devices have different thicknesses of PZT installed on a substrate, where there are stepped differences. Vibrators of low resonant frequency are installed on the lower stages, and vibrators of high resonant frequency are installed on the upper stages.

Then, an acoustic matching layer is arranged so as to overlap the respective vibrators. Where the opposite side of the vibrators is understood to be the front surface, the acoustic matching layer has a front surface that is formed so as to be flat. Having a flat front surface makes it possible to easily make contact with a test subject. The thickness of the acoustic matching layer and the thickness of the vibrators are set so as to correspond to the resonant frequency. The difference in length found by adding both the thickness of the acoustic matching layer and the thickness of the vibrators will be the height of the stepped differences of the substrate. As such, providing the stepped differences to the substrates makes it possible to properly set both the lengths of the vibrators and the length of the acoustic matching layer even though the front surface is a flat one.

SUMMARY

In Japanese Laid-Open Patent Publication No. H2-49640, the stepped differences of the substrate correspond to elements of the vibrators, and therefore the number of stepped differences is increased by an amount commensurate with any increase in the number of vibrators. As such, the substrate is more difficult to manufacture in an ultrasonic device of a structure where many vibrators are arranged on the substrate. Therefore, there has been a desire for an ultrasonic device of a structure that is easy to manufacture even when there are many pluralities of vibrators having different resonant frequencies arranged thereon.

The present invention has been made in order to solve this problem, and can be implemented as the following aspects.

An ultrasonic device according to one aspect includes a substrate, a first piezoelectric body, a second piezoelectric body, and an acoustic matching section. The substrate has a first surface that is a flat surface. The first piezoelectric body is disposed on the first surface of the substrate. The second piezoelectric body is disposed on the first surface of the substrate. The second piezoelectric body has a different thickness from a thickness of the first piezoelectric body as measured from the first surface of the substrate. The acoustic matching section is disposed on the first piezoelectric body and the second piezoelectric body. The acoustic matching section has a first side facing the first piezoelectric body and the second piezoelectric body, and a second side opposite from the first side. A surface of the acoustic matching section on the second side is a flat surface parallel with the first surface of the substrate.

According to this aspect, the ultrasonic device is provided with the first piezoelectric body and the second piezoelectric body on the substrate. Applying an alternating current voltage causes the first piezoelectric body to emit ultrasonic waves. The acoustic matching section is provided onto the first piezoelectric body and the second piezoelectric body. The emitted waves pass through the acoustic matching section and are emitted into a test subject. Reflected in the test subject, the ultrasonic waves pass through the acoustic matching section and are incident on the second piezoelectric body. With the acoustic matching section, the acoustic impedance is adjusted and therefore the ultrasonic waves can efficiently travel through between the first piezoelectric body, the test subject, and the second piezoelectric body.

The ultrasonic waves are incident on the second piezoelectric body, which then output a signal of an alternating current voltage. Because the first piezoelectric body and the second piezoelectric body have different thicknesses, the resonant frequencies of each of the piezoelectric bodies are different frequencies. As such, the ultrasonic device emits the ultrasonic waves toward the test subject from the first piezoelectric body, and the second piezoelectric body is able to detect ultrasonic waves of a different frequency out of the ultrasonic waves that are reflected in the test subject. Then, the first surface where the first piezoelectric body and the second piezoelectric body are installed in the substrate is a flat surface. The surface on the second side of the acoustic matching section opposite to the first piezoelectric body and the second piezoelectric body is also a flat surface. As such, the substrate has a shape that facilitates processing compared to when unevenness is provided to the first surface. The acoustic matching section has a shape that facilitates processing compared to when unevenness is provided to the surface on the second side. As a result, the ultrasonic device can be manufactured at high productivity.

In the ultrasonic device according to the aspect, the following formulae (1) to (7) are preferably satisfied, where Cp is a speed of sound in the first piezoelectric body and the second piezoelectric body, Cs is a speed of sound in the acoustic matching section, f1 is a resonant frequency of the first piezoelectric body, f2 is a resonant frequency of the second piezoelectric body, d1 is the thickness of the first piezoelectric body, d2 is the thickness of the second piezoelectric body, t1 is a thickness of the acoustic matching section as measured from a surface of the first piezoelectric body, t2 is a thickness of the acoustic matching section as measured from a surface of the second piezoelectric body, n is an integer, and k1 and k2 are odd numbers.

$$f2 = n \times f1 \qquad \text{formula (1)}$$

$$d1 = Cp/(2 \times f1) \qquad \text{formula (2)}$$

$$d2 = Cp/(2 \times f2) \qquad \text{formula (3)}$$

$$t1=k1\times Cs/(4\times f1) \quad \text{formula (4)}$$

$$t2=k2\times Cs/(4\times f2) \quad \text{formula (5)}$$

$$d1+t1=d2+t2 \quad \text{formula (6)}$$

$$Cs=2\times(n-1)\times Cp(k2-n\times k1) \quad \text{formula (7)}$$

According to this aspect, as illustrated in the formula (1), the resonant frequency of the second piezoelectric body will be an integer multiple of the resonant frequency of the first piezoelectric body. As such, the first piezoelectric body outputs ultrasonic waves, and the second piezoelectric body can detect an n-th order of higher frequency of ultrasonic waves reflected in the test subject. Having the thickness d1 of the first piezoelectric body be as illustrated in the formula (2) makes it possible to have the resonant frequency of the first piezoelectric body be the resonant frequency f1. Likewise, having the thickness d2 of the second piezoelectric body be as illustrated in the formula (3) makes it possible to have the resonant frequency of the second piezoelectric body be the resonant frequency f2.

When the wavelength and frequency of the ultrasonic waves traveling through the acoustic matching section are $\lambda$ and f, respectively, then there is a relationship $\lambda=Cs/f$. As such, the formula (4) illustrates $t1=k1\times\lambda/4$, and the formula (5) illustrates $t2=k2\times\lambda/4$. That is to say, the thickness of the acoustic matching section is an odd multiple of $\lambda/4$. Because being an odd multiple of $\lambda/4$ is a wavelength matching condition, any incidence where the ultrasonic waves traveling through the acoustic matching section would cancel each other out with the ultrasonic waves reflected in the interface of the acoustic matching section is curbed. As such, the acoustic matching section can allow the ultrasonic waves to travel through efficiently.

As illustrated by the formula (6), the thickness obtained by adding the thickness of the first piezoelectric body and the thickness of the acoustic matching section that is on the first piezoelectric body is made to be the same thickness as the thickness obtained by adding the thickness of the second piezoelectric body and the thickness of the acoustic matching section thickness that is on the second piezoelectric body. This makes it possible to flatten the first surface, which is where the first piezoelectric body and the second piezoelectric body are installed in the substrate, and also to flatten the surface on the second side of the acoustic matching section opposite to the first piezoelectric body and the second piezoelectric body in the acoustic matching section. Then, the formula (7) is derived from the formulae (1) to (6). Cs is computed by setting n, k1, k2, and Cp as illustrated by the formula (7). Then, a material with which the speed of sound corresponds to the computed Cs is selected for the material of the acoustic matching section. As such, an ultrasonic device with which the ultrasonic waves efficiently travel through the acoustic matching section can be manufactured at high productivity.

In the ultrasonic device as in the above-described aspect, the acoustic matching section is preferably made of natural rubber.

According to this aspect, the material of the acoustic matching section is natural rubber. In the formula (7) of the application example 2, Cs can be made to be 1600 m/s when n=2, k1=1, k2=7, and Cp=4000 m/s. Then, the natural rubber fits for when Cs=1600 m/s. Natural rubbers have excellent workability. As such, using a natural rubber for the material of the acoustic matching section makes it possible to manufacture at high productivity an ultrasonic device with which the ultrasonic waves travel efficiently through the acoustic matching section.

In the ultrasonic device as in the above-described aspect, the acoustic matching section is preferably made of silicone resin.

According to this aspect, the material of the acoustic matching section is silicone resin. In the formula (7) of the application example 2, Cs can be made to be 1143 m/s when n=2, k1=1, k2=9, and Cp=4000 m/s. Then, the silicone resin fits for when Cs=1143 m/s. Silicone resins have excellent workability. As such, using a silicone resin for the material of the acoustic matching section makes it possible to manufacture at high productivity an ultrasonic device with which the ultrasonic waves travel efficiently through the acoustic matching section.

In the ultrasonic device as in the above-described aspect, the acoustic matching section is preferably made of polyethylene resin.

According to this aspect, the material of the acoustic matching section is polyethylene resin. In the formula (7) of the application example 2, Cs can be made to be 2000 m/s when n=3, k1=1, k2=11, and Cp=4000 m/s. Then, the polyethylene resin fits for when Cs=2000 m/s. Polyethylene resins have excellent workability. As such, using a polyethylene resin for the material of the acoustic matching section makes it possible to manufacture at high productivity an ultrasonic device with which the ultrasonic waves travel efficiently through the acoustic matching section.

A method of manufacturing an ultrasonic device according to another aspect includes: forming a first piezoelectric body and a second piezoelectric body on a flat first surface of a substrate; and forming an acoustic matching section having a first side facing the first piezoelectric body and the second piezoelectric body, and a second side opposite from the first side, so that a surface of the acoustic matching section on the second side is a flat surface parallel with the first surface of the substrate.

According to the present application example, the first piezoelectric body and the second piezoelectric body are formed on the substrate. The first surface of the substrate, onto which the first piezoelectric body and the second piezoelectric body are provided, is flat and can be easily processed. The acoustic matching section is formed on the first piezoelectric body and the second piezoelectric body. The surface on the second side of the acoustic matching section opposite to the first piezoelectric body and the second piezoelectric body is flat. As such, the first surface of the substrate and the surface on the second side of the acoustic matching section can both be produced at high productivity.

An ultrasonic probe according to another aspect includes an ultrasonic device, and a drive section configured and arranged to drive the ultrasonic device. The ultrasonic device includes a substrate, a first piezoelectric body, a second piezoelectric body, and an acoustic matching section. The substrate has a first surface that is a flat surface. The first piezoelectric body is disposed on the first surface of the substrate. The second piezoelectric body is disposed on the first surface of the substrate. The acoustic matching section is disposed on the first piezoelectric body and the second piezoelectric body. The acoustic matching section has a first side facing the first piezoelectric body and the second piezoelectric body, and a second side opposite from the first side. A surface of the acoustic matching section on the second side is a flat surface parallel with the first surface of the substrate.

According to this aspect, the ultrasonic probe is provided with the ultrasonic device and the drive section. The drive section drives the ultrasonic device. In the ultrasonic device, the first surface onto which the first piezoelectric body and the second piezoelectric body are provided in the substrate is a flat surface. The surface on the second side of the acoustic matching section opposite to the first piezoelectric body and the second piezoelectric body is also a flat surface. As such, the substrate has a shape that facilitates processing compared to when unevenness is provided to the first surface. The acoustic matching section has a shape that facilitates processing compared to when unevenness is provided to the surface on the second side. As a result, an ultrasonic probe can be made into an ultrasonic probe provided with an ultrasonic device that can be manufactured at high productivity.

An ultrasonic diagnostic apparatus according to another aspect includes an ultrasonic device, a drive section, a reflection distribution computation section, and a display section. The ultrasonic device is configured and arranged to emit ultrasonic waves at a test subject and to detect ultrasonic waves that are reflected in the test subject. The drive section is configured and arranged to drive the ultrasonic device. The reflection distribution computation section is configured to compute distribution of reflectance of ultrasonic waves in the test subject from the ultrasonic waves detected by the ultrasonic device. The display section is configured and arranged to display an image based on the distribution of reflectance of ultrasonic waves in the test subject as computed by the reflection distribution computation section. The ultrasonic device includes a substrate, a first piezoelectric body, a second piezoelectric body, and an acoustic matching section. The substrate has a first surface that is a flat surface. The first piezoelectric body is disposed on the first surface of the substrate. The second piezoelectric body is disposed on the first surface of the substrate. The acoustic matching section is disposed on the first piezoelectric body and the second piezoelectric body. The acoustic matching section has a first side facing the first piezoelectric body and the second piezoelectric body, and a second side opposite from the first side. A surface of the acoustic matching section on the second side is a flat surface parallel with the first surface of the substrate.

According to this aspect, the ultrasonic diagnostic apparatus is provided with the ultrasonic device, the drive section, the reflection distribution computation section, and the display section. The drive section drives the ultrasonic device. The ultrasonic device emits ultrasonic waves at the test subject, and detects ultrasonic waves that are reflected in the test subject. The reflection distribution computation section computes the distribution of reflectance of ultrasonic waves in the test subject from the ultrasonic waves that are detected by the ultrasonic device. The display section displays the distribution of reflectance of ultrasonic waves in the test subject as computed by the reflection distribution computation section. An operator can know the distribution of reflectance of ultrasonic waves in the interior of the test subject by looking at the display section.

In the ultrasonic device, the first surface onto which the first piezoelectric body and the second piezoelectric body are provided in the substrate is a flat surface. The surface on the second side of the acoustic matching section opposite to the first piezoelectric body and the second piezoelectric body is also flat. As such, the substrate has a shape that facilitates processing compared to when unevenness is provided to the first surface. The acoustic matching section has a shape that facilitates processing compared to when unevenness is provided to the surface on the second side. As a result, an ultrasonic diagnostic apparatus can be made into an ultrasonic diagnostic apparatus provided with an ultrasonic device that can be manufactured at high productivity.

BRIEF DESCRIPTION OF THE DRAWINGS

Referring now to the attached drawings which form a part of this original disclosure:

FIG. 4 is a drawing illustrating the result of material selection for when harmonic imaging has an order of n=2;

FIG. 5 is a drawing illustrating the result of material selection for when harmonic imaging has an order of n=3;

FIGS. 10A to 109F are schematic diagrams for describing a method of manufacturing an ultrasonic sensor.

DETAILED DESCRIPTION OF EXEMPLARY EMBODIMENTS

The present embodiment describes an example of an ultrasonic device having a characteristic structure, as well as an ultrasonic probe and ultrasonic image apparatus provided with this ultrasonic device. Embodiments shall be described below, with reference to the accompanying drawings. Each of the members in each of the drawings is given a size large enough to be recognizable on each of the drawings, and therefore every member is depicted with a different dimensional scale.

First Embodiment

Figure 1A:
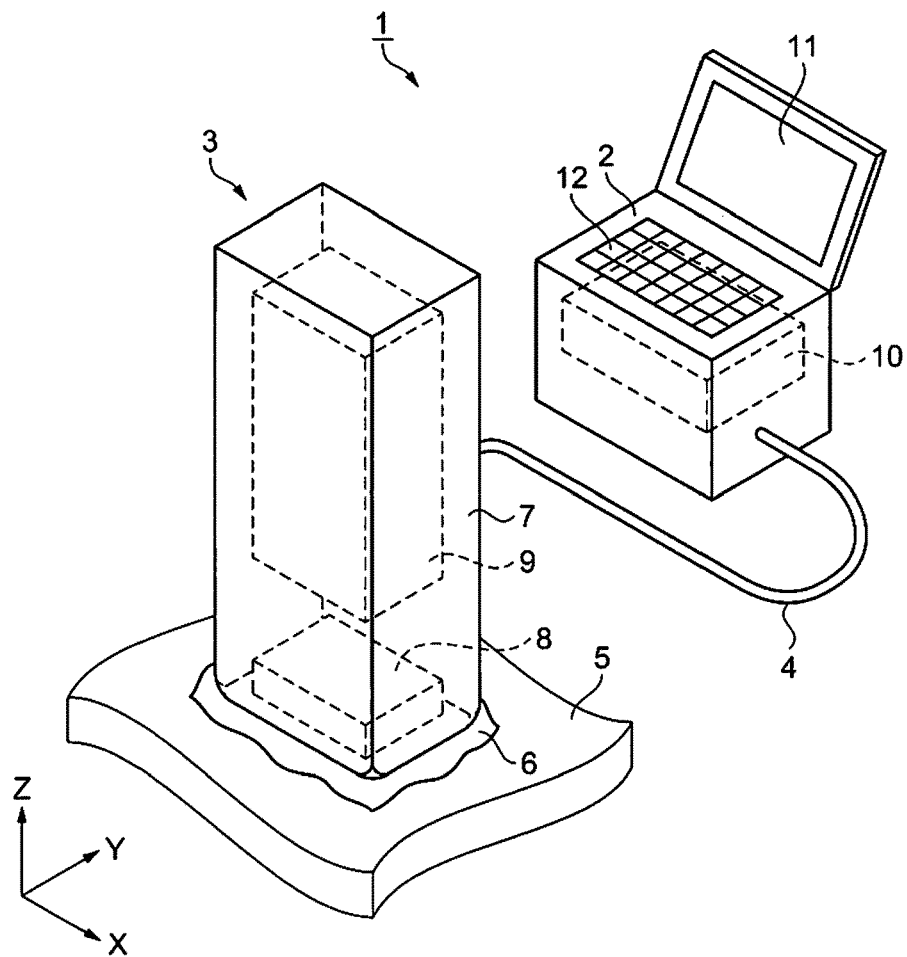
FIG. 1A is a schematic perspective view illustrating a structure of an ultrasonic image apparatus and FIG. 1B is a schematic perspective view illustrating a structure of an ultrasonic sensor according to a first embodiment.

An ultrasonic image apparatus as in a first embodiment shall now be described with reference to FIGS. 1 to 7. FIG. 1A is a schematic perspective view illustrating the structure of the ultrasonic image apparatus. As illustrated in FIG. 1A, an ultrasonic image apparatus 1 is provided with an image processing apparatus 2 and an ultrasonic probe 3. The image processing apparatus 2 and the ultrasonic probe 3 are connected by a cable 4. The ultrasonic probe 3 is used by being pressed against a test subject 5. The surface of the test subject 5 is coated with a liquid body 6, and the liquid body 6 is interposed between the ultrasonic probe 3 and the test subject 5. The liquid body 6 is endowed with the function of conducting and not reflecting ultrasonic waves emitted by the ultrasonic probe 3.

The ultrasonic probe 3 is provided with an exterior covering section 7. The shape of the exterior covering section 7 is a bottomed square tube. An ultrasonic sensor 8 is installed on the exterior covering section 7, on a side facing the test subject 5, and the ultrasonic waves are emitted toward the test subject 5 from the ultrasonic sensor 8. The ultrasonic waves are reflected in the interior of the test subject 5. The ultrasonic sensor 8 detects the reflected waves reflected in the interior of the test subject 5. The interior of the exterior covering section 7 houses a sensor drive section 9 serving as a drive section for driving the ultrasonic sensor 8.

The image processing apparatus 2 is provided with an image computation section 10 serving as a reflection distribution computation section, an image display section 11 serving as a display section, and an input section 12. The image computation section 10 uses a reflected wave signal outputted by the ultrasonic probe 3, to compute the distribution of reflectance in a cross-section of the test subject 5. Then, a cross-sectional image is computed from the result of computation of the distribution of reflectance, and outputted to the image display section 11. The image display section 11 receives the input of the result of computation outputted by the image computation section 10, and displays the cross-sectional image of the test subject 5. The cross-sectional image displays the distribution of reflectance. The input section 12 is a site where command content is inputted to the ultrasonic image apparatus 1 by an operator.

The longitudinal direction of the ultrasonic probe 3 is understood here to be the Z-direction. For greater detail, the direction in which the ultrasonic probe 3 faces the test subject 5 is understood to be the −Z-direction. The two orthogonal directions on the plane where the ultrasonic probe 3 and the test subject 5 are in contact are understood to be the X-direction and the Y-direction. The X-direction, the Y-direction, and the Z-direction are each respectively orthogonal directions.

Figure 1B:
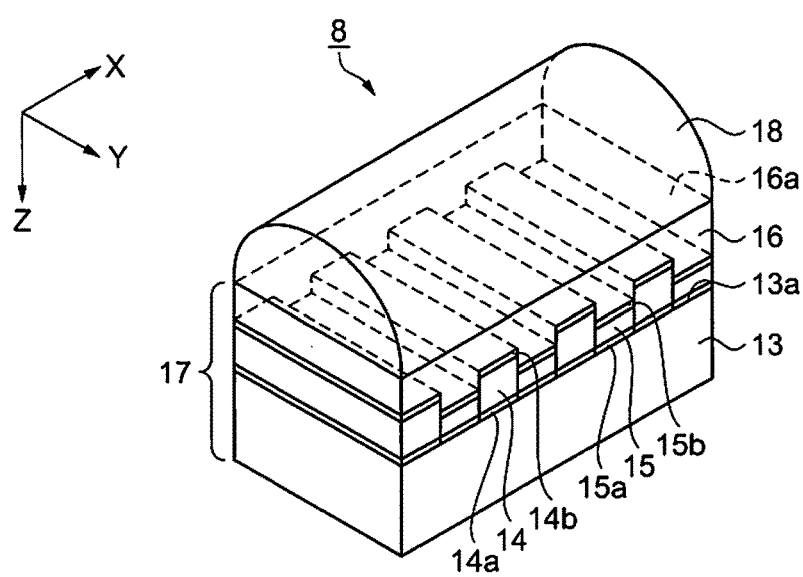

FIG. 1B is a schematic perspective view illustrating a structure of an ultrasonic sensor. As illustrated in FIG. 1B, the ultrasonic sensor 8 is provided with a rectangular substrate 13. The material of the substrate 13 is not particularly limited, provided that the material has a high acoustic attenuation. This material is referred to as a backing material. The substrate 13 is formed by, for example, mixing a powder of metal, ferrite, ceramic, or the like into an elastic member made of an epoxy resin, rubber, or the like.

In the substrate 13, the surface facing the −Z-direction is understood to be a first surface 13a. The first surface 13a is a flat surface. First piezoelectric bodies 14 and second piezoelectric bodies 15 are arranged alternately side by side on the first surface 13a. The shape of the first piezoelectric bodies 14 is a prism, and first electrodes 14 are installed on a surface of the first piezoelectric bodies 14 facing the substrate 13 side Second electrodes 14b are installed on surfaces of the opposite side to the first electrodes 14a in the first piezoelectric bodies 14.

The shape of the second piezoelectric bodies 15 is a prism, and the length of the second piezoelectric bodies 15 in the Y-direction is the same as the length of the first piezoelectric bodies 14. The length of the X-direction width of the second piezoelectric bodies 15 is also the same as the length of the first piezoelectric bodies 14. The length of the Z-direction thickness of the second piezoelectric bodies 15 is shorter than the length of the first piezoelectric bodies 14. First electrodes 15a are installed on a surface of the second piezoelectric bodies 15 facing the substrate 13 side. Second electrodes 15b are installed on a surface of the opposite side to the first electrodes 15a in the second piezoelectric bodies 15.

For the sake of simplifying the drawings, the depicted first piezoelectric bodies 14 and second piezoelectric bodies 15 are arranged each in increments of four. The numbers of first piezoelectric bodies 14 and second piezoelectric bodies 15 are not particularly limited. When the numbers are greater, the examination range can be widened by a commensurate amount. Alternatively, the resolution can be increased. In the present embodiment, for example, there are 256 of the first piezoelectric bodies 14 and the second piezoelectric bodies 15, each.

The materials of the first piezoelectric bodies 14 and second piezoelectric bodies 15 are not particularly limited, provided that the material be one where an alternative current voltage is applied and ultrasonic waves are emitted. For the materials of the first piezoelectric bodies 14 and the second piezoelectric bodies 15, it would be possible to use piezoelectric elements such as lead (Pb) zirconium titanate (PZT) elements or polyvinylidene fluoride (PDVF) elements. In the present embodiment, PZT elements, which are one kind of piezoelectric element, are used. The first piezoelectric bodies 14 and the second piezoelectric bodies 15 are also called acoustic transducers.

When an alternating current voltage is applied between the first electrodes 14a and the second electrodes 14b, then the first piezoelectric bodies 14 emit ultrasonic waves. The first piezoelectric bodies 14 function as elements for emitting ultrasonic waves. The second piezoelectric bodies 15 receive incident ultrasonic waves and generate an alternating current voltage between the first electrodes 15a and the second electrodes 15b. The second piezoelectric bodies 15 function as elements for detecting the ultrasonic waves. Thicker piezoelectric bodies can emit ultrasonic waves of lower frequency and detect ultrasonic waves of lower frequency than thinner piezoelectric bodies The second piezoelectric bodies 15 are set so as to be thinner than the first piezoelectric bodies 14. This results in the second piezoelectric bodies 15 detecting ultrasonic waves of a frequency higher than the ultrasonic waves emitted by the first piezoelectric bodies 14.

The surfaces of the first electrodes 14a and first electrodes 15a that face the substrate 13 are flat. The first electrodes 14a are fixed by adhesion to the first surface 13a, and the first electrodes 15a are also fixed by adhesion to the first surface 13a.

An acoustic matching section 16 is installed on the −Z-direction side of the first piezoelectric bodies 14 and second piezoelectric bodies 15. The acoustic matching section 16 has the function of matching the acoustic impedance between the first piezoelectric bodies 14 and second piezoelectric bodies 15 and the test subject 5. In the acoustic matching section 16, the surface facing the −Z-direction is understood to be a second surface 16a (i.e., a surface on the second side of the acoustic matching section 16). The second surface 16a is a flat surface.

The materials for the first electrodes 14a, the second electrodes 14b, the first electrodes 15a, and the second electrodes 15b are not particularly limited, provided that the materials be electroconductive. It would be possible to a metal such as gold, silver, copper, nickel, or aluminum, an alloy of these metals, or laminated metal.

A portion going from the substrate 13 to the acoustic matching section 16 is understood to be an ultrasonic device 17. The ultrasonic device 17 encompasses the substrate 13, the first piezoelectric bodies 14, the first electrodes 14a, the second electrodes 14b, the second piezoelectric bodies 15, the first electrodes 15a, the second electrodes 15b, and the acoustic matching section 16.

An acoustic lens 18 is attached to the second surface 16a. The acoustic lens 18 is a column lens extending in the X-direction, with which the same as seen from the X-direction is convex. The acoustic lens 18 is also called a rod lens. The ultrasonic waves emitted from the first piezoelectric bodies 14 pass through the acoustic matching section 16 and are incident on the acoustic lens 18. The ultrasonic waves are focused by the acoustic lens 18. A material with which the speed of sound of travel through the acoustic lens 18 is slower than the test subject 5 is used for the material of the acoustic lens 18. For example, where the test subject 5 is a human body, silicone rubber could be used for the material of the acoustic lens 18.

Figure 2A:
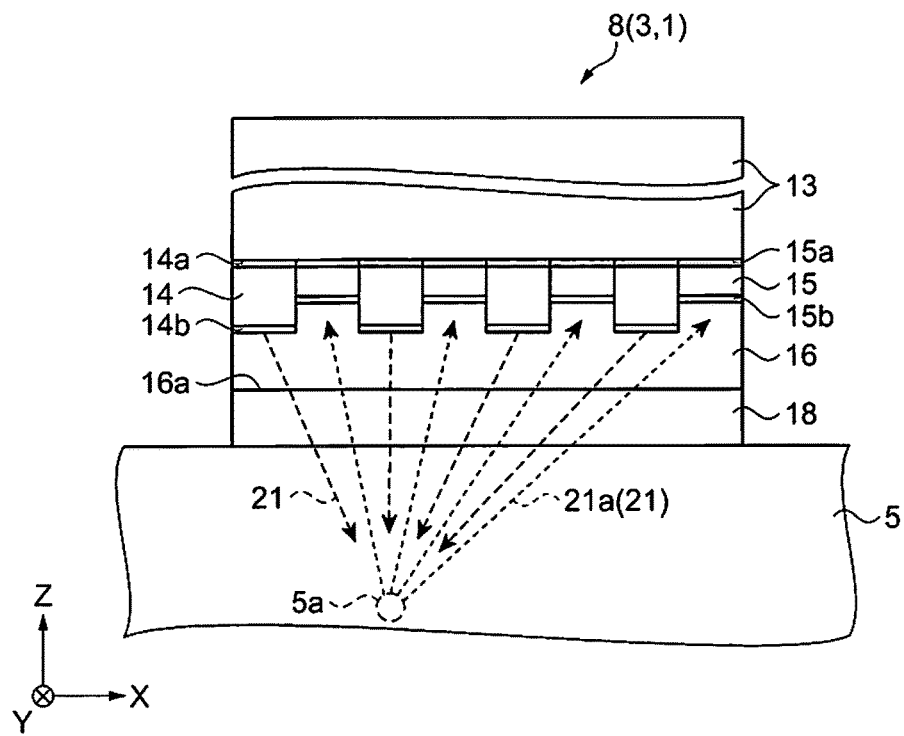
FIG. 2A is a schematic diagram for describing emission and detection of ultrasonic waves in an ultrasonic sensor.

FIG. 2A is a schematic diagram for describing the emission and detection of the ultrasonic waves in the ultrasonic sensor. As illustrated in FIG. 2A, ultrasonic waves 21 are emitted from the plurality of first piezoelectric bodies 14. The emitted ultrasonic waves 21 pass through the acoustic matching section 16 and the acoustic lens 18 and are incident on the test subject 5. The arrayed first piezoelectric bodies 14 emit the ultrasonic waves 21 with respectively different phases. The location on the test subject 5 that is being examined is understood to be an examination point 5a. The ultrasonic waves 21 emitted from each of the first piezoelectric bodies 14 are emitted so as to be in the same phase at the examination point 5a. At the examination point 5a, the ultrasonic waves 21 interfere constructively, and therefore the same effect as the focusing by the acoustic lens 18 or the like is obtained.

The ultrasonic waves 21 that are reflected in the examination point 5a are understood to be reflected waves 21a. The reflected waves 21a pass through the test subject 5, the acoustic lens 18, and the acoustic matching section 16 and are incident on the second piezoelectric bodies 15. Because there is a different distance between the examination point 5a and each of the second piezoelectric bodies 15, the reflected waves 21a detected by each of the second piezoelectric bodies 15 will have waveforms of different phases. The sensor drive section 9 computes the intensity of the reflected waves 21a that are reflected in the examination point 5a by adjusting the phase of the reflected waves 21a. The ultrasonic probe 3 modifies the phase of the ultrasonic waves emitted by the first piezoelectric bodies 14 and causes the examination point 5a to move in the X-direction. Then, the intensity of the reflected waves 21a at each location is computed. The ultrasonic image apparatus 1 thereby computes the distribution of intensity of the reflected waves 21a in the interior of the test subject 5.

The frequency of the ultrasonic waves 21 emitted by the first piezoelectric bodies 14 is understood to be f1. The reflected waves 21a include sound waves of frequencies that are integer multiples of f1. The straightness of travel by the reflected waves 21a is better when the frequency is higher, and therefore an image obtained by analyzing reflected waves 21a of a high frequency will have a higher spatial resolution. When the frequency is higher, also, the sound pressure becomes lower, and therefore detection becomes more difficult. Accordingly, efficiently moving the ultrasonic waves higher in the acoustic matching section 16 becomes increasingly important. The second piezoelectric bodies 15 are thinner than the first piezoelectric bodies 14 and therefore are able to detect reflected waves 21a of a higher frequency than f1. Where the frequency detected relative to f1 is n-fold, then n is referred to as the order of harmonic imaging.

Figure 2B:
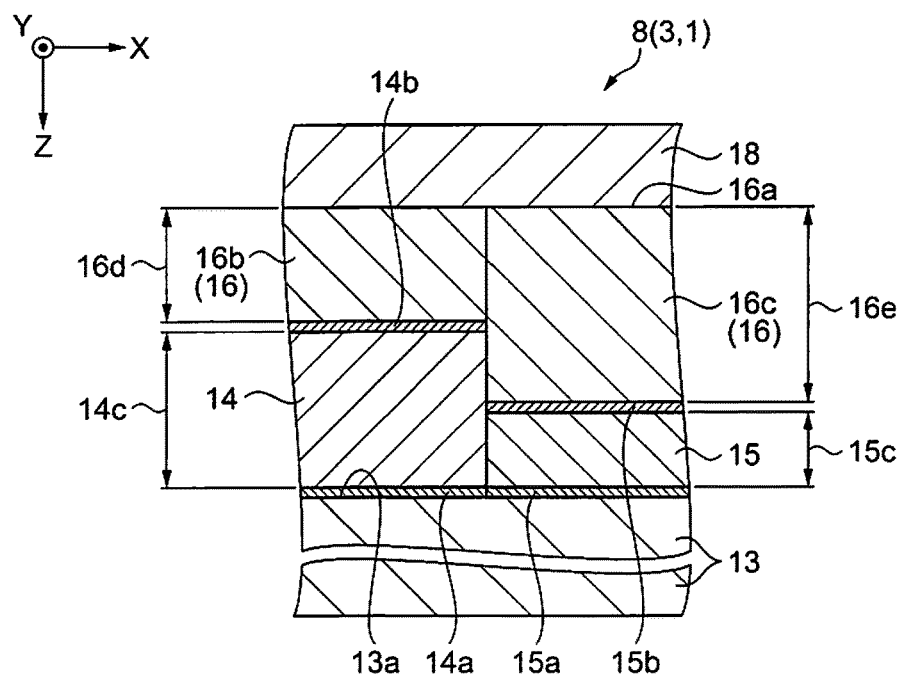
FIG. 2B is a schematic diagram for describing the relationship between the dimensions of an acoustic matching section and a piezoelectric body.

FIG. 2B is a schematic diagram for describing the relationship between the dimensions of the acoustic matching section and the piezoelectric bodies. As illustrated in FIG. 2B, the acoustic matching section 16 located on the −Z-side of the first piezoelectric bodies 14 is understood to be a first acoustic matching section 16b. The acoustic matching section 16 that is located on the −Z-side of the second piezoelectric bodies 15 is understood to be a second acoustic matching section 16c.

The first surface 13a and the second surface 16a are flat surfaces, and are parallel surfaces. The first electrodes 14a and the first electrodes 15a are the same thickness; and the second electrodes 14b and the second electrodes 15b are the same thickness. The thickness of the first piezoelectric bodies 14 is understood to be a first piezoelectric body thickness 14c and the thickness of the first acoustic matching section 16b is understood to be a first acoustic matching section thickness 16d. The thickness of the second piezoelectric bodies 15 is understood to be a second piezoelectric body thickness 15c and the thickness of the second acoustic matching section 16c is understood to be a second acoustic matching section thickness 16e. At this time, the thickness obtained by adding the first piezoelectric body thickness 14c and the first acoustic matching section thickness 16d will be the same thickness as the thickness obtained by adding the second piezoelectric body thickness 15c and the second acoustic matching section thickness 16e.

Next, the selection of the material of the acoustic matching section 16 shall be described, as shall a method of setting the first acoustic matching section thickness 16d and the second acoustic matching section thickness 16e. Where the wavelength of the ultrasonic waves 21 traveling through the acoustic matching section 16 is λ, then the first acoustic matching section thickness 16d and the second acoustic matching section thickness 16e are set to an odd multiple of ¼×λ. This makes it possible to reduce the amount to which the ultrasonic waves 21 are reflected in the interface. As such, any reduction in sound pressure in passing through the acoustic matching section 16 can be curbed, and the reflected waves 21a can be efficiently detected.

A condition for having the first surface 13a and the second surface 16a be flat is satisfied. Namely, the thickness obtained when the first piezoelectric body thickness 14c and the first acoustic matching section thickness 16d are added is set to the same thickness as the thickness obtained when the second piezoelectric body thickness 15c and the second acoustic matching section thickness 16e are added. The first piezoelectric body thickness 14c is understood to be d1, and the first acoustic matching section thickness 16e is understood to be t1. The second piezoelectric body thickness 15c is understood to be d2, and the second acoustic matching section thickness 16e is understood to be t2. At this time, the following formula (1) must be satisfied.

$$d1+t1=d2+t2 \qquad \text{formula (1)}$$

The materials for the first piezoelectric bodies 14 and the second piezoelectric bodies 15 are understood to both be the same material. The speed of sound in passing through the first piezoelectric bodies 14 and the second piezoelectric bodies 15 is understood to be Cp. The resonant frequency of the first piezoelectric bodies 14 is understood to be f1. At this time, the relationship in the following formula (2) holds true.

$$d1=Cp/(2 \times f1) \qquad \text{formula (2)}$$

The resonant frequency detected by the second piezoelectric bodies 15 is understood to be f2. f2 is a frequency of an integer multiple of f2, and the integer of the integer multiple is understood to be n. At this time, the relationships in the following formulae (3) to (5) hold true.

$$d2=Cp/(2\times f2) \quad \text{formula (3)}$$

$$f2=n\times f1 \quad \text{formula (4)}$$

$$d2=Cp/(2\times n\times f1) \quad \text{formula (5)}$$

The speed of sound of the ultrasonic waves 21 when passing through the acoustic matching section 16 is understood to be Cs. The frequency of the ultrasonic waves 21 emitted by the first piezoelectric bodies 14 is f1. The wavelength of the ultrasonic waves 21 when passing through the first acoustic matching section 16b is understood to be λ1. k1 is understood to be an odd number. At this time, the relationships in the following formulae (6) to (8) hold true.

$$\lambda 1=Cs/f1 \quad \text{formula (6)}$$

$$t1=k1\times\lambda 1/4 \quad \text{formula (7)}$$

$$t1=k1\times Cs/(4\times f1) \quad \text{formula (8)}$$

The wavelength of the reflected waves 21a passing through the second acoustic matching section 16c is understood to be λ2. k2 is understood to be an odd number. At this time, the relationships in the following formulae (9) to (12) hold true.

$$\lambda 2=Cs/f2 \quad \text{formula (9)}$$

$$t2=k2\times\lambda 2/4 \quad \text{formula (10)}$$

$$t2=k2\times Cs/(4\times f2) \quad \text{formula (11)}$$

$$t2=k2\times Cs/(4\times n\times f1) \quad \text{formula (12)}$$

Formula (2), formula (5), formula (8), and formula (12) are plugged into formula (1) and d1,d2, t1, and t2 are eliminated. As a result of this operation, the relationship in the following formula (13) holds true. The formula (14) is derived by transforming the formula (13).

$$k2=n\times k1+2\times(n-1)\times Cp/Cs \quad \text{formula (13)}$$

$$Cs=2\times(n-1)\times Cp/(k2-n\times k1) \quad \text{formula (14)}$$

In formula (14), setting n, k1, k2, and Cp makes it possible to compute Cs. Cs is a value inherent to the material of the acoustic matching section 16. Selected for the material of the acoustic matching section 16 is a material where the speed of sound matches or approximates the computed value of Cs. When no suitable material exists, then n, k1, and/or k2 are modified and Cs is recomputed to select a suitable material. The procedure for this operation shall be described next.

Figure 3:
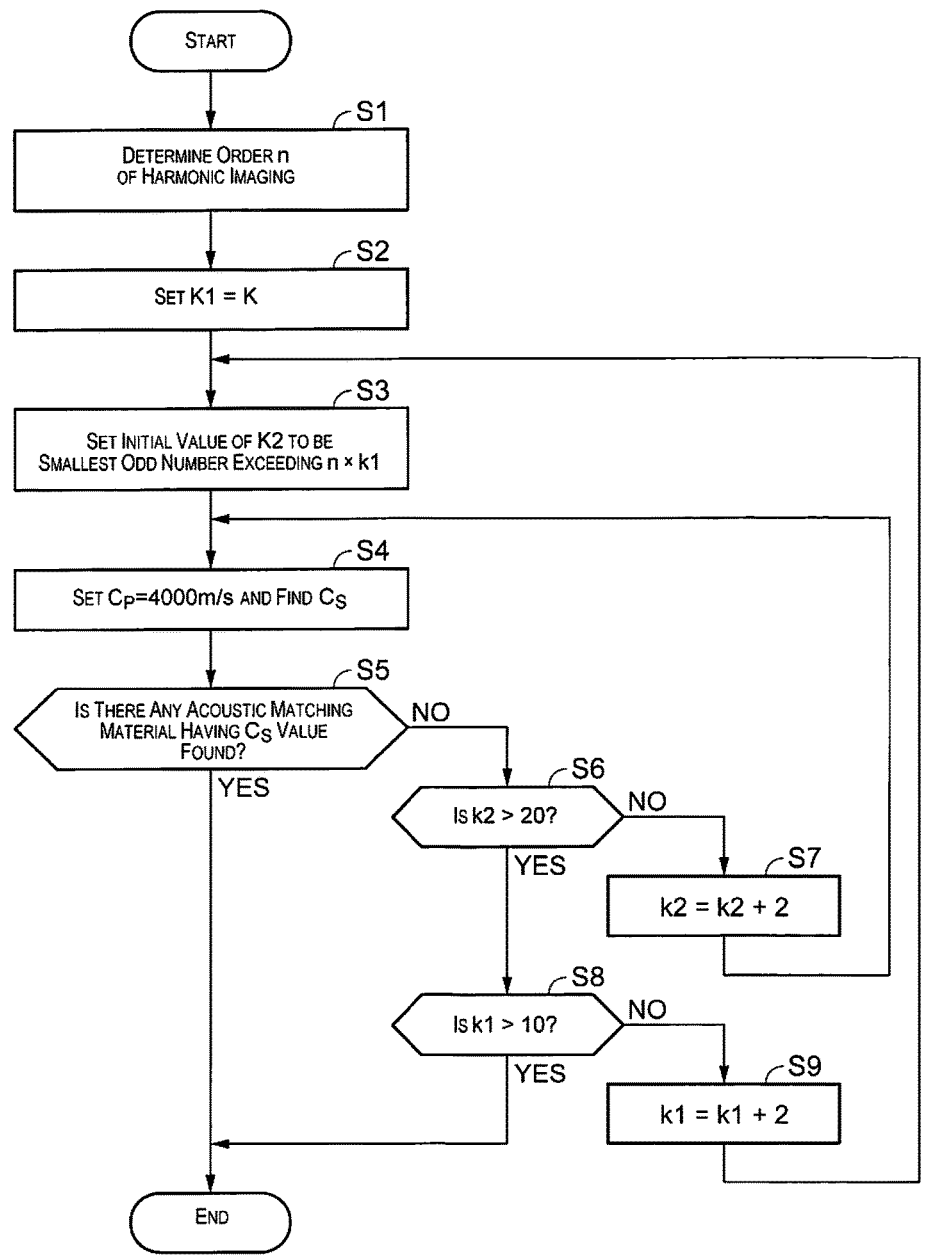
FIG. 3 is a flowchart for describing the procedure for selecting the material of an acoustic matching section.

FIG. 3 is a flowchart for describing the procedure for selecting the material of the acoustic matching section. A step S1 corresponds to a step for "determining the order n of harmonic imaging". In this step, the order n of harmonic imaging is set. The order n is an integer 2 or higher. Next is a transition to a step S2. The step S2 corresponds to a step for "setting k1=1". This step is a step where the initial value of k1 is set to 1. Next is a transition to a step S3.

The step S3 corresponds to a step for "setting the initial value of k2 a minimum odd number greater than n×k1". This step is a step where the initial value of k2 is set. When n=2 and k1=1, then k2 is set to =3. When n=3 and k1=1, then k2 is set to =5. Next is a transition to a step S4. The step S4 corresponds to a step for "finding Cs where Cp=4000 m/s". The material for the first piezoelectric bodies 14 and the second piezoelectric bodies 15 is understood to be PZT. Cp is the speed of sound in PZT. This step is a step where n, k1, k2, and Cp are plugged into the formula (13) and Cs is computed. Next is a transition to a step S5.

The step S5 corresponds to a step for determining "is there any acoustic matching material that has the Cs value needed?". This step is a step where the acoustic matching material is set. When a suitable acoustic matching material can be set, then this corresponds to YES, and the procedure for selecting the material for the acoustic matching section 16 is concluded. When a suitable acoustic matching material cannot be set, then this corresponds to NO, and the flow next transitions to a step S6.

The step S6 corresponds to a step for determining "is k2>20?". The upper limit of k2 is set to 20, and this step is a step where the question of whether the value of k2 exceeds the upper limit is determined. When the value of k2 exceeds the upper limit, then this corresponds to YES, and the flow next proceeds to a step S8. When the value of k2 does not exceed the upper limit, then this corresponds to NO, and the flow next proceeds to a step S7.

The step S7 corresponds to a step for setting "k2=k2+2". This step is a step where the integer 2 is added to k2. k2 after the addition will be an odd number. Next is a transition to the step S4.

The step S8 corresponds to a step for determining whether "k1>10?". The upper limit of k1 is set to 10, and this step is a step where the question of whether the value of k1 exceeds the upper limit is determined. When the value of k1 exceeds the upper limit, then this corresponds to YES, and the procedure for setting the material of the acoustic matching section 16 is concluded. When the value of k1 does not exceed the upper limit, then this corresponds to NO, and the flow next proceeds to a step S9. In a case where k2>20 or where k1>10, then the thickness of the acoustic matching section 16 ends up being dominant over the thickness of the first piezoelectric bodies 14 and the second piezoelectric bodies 15. For this reason, the concern is that this is no longer conducive to reducing the scale of the ultrasonic probe 3, and it does not signify that the acoustic matching conditions are lost.

The step S9 corresponds to a step for setting "k1=k1+2". This step is a step where the integer 2 is added to k1. k1 after the addition will be an odd number. Next is a transition to the step 3. This concludes the description of the procedure for selecting the material for the acoustic matching section 16. When a suitable material for the acoustic matching section 16 cannot be selected by carrying out n=2, then the material for the acoustic matching section 16 is selected by setting n=3 or higher.

FIG. 4 is a drawing illustrating the result of material selection for when the order n of harmonic imaging=2. As illustrated in FIG. 4, PZT is selected for the material for the first piezoelectric bodies 14 and the second piezoelectric bodies 15, and n=2 is selected. When k1=1 and k2=3, then Cs=8000 m/s. The materials corresponding to this Cs are limited to special metals, such as beryllium. The acoustic impedance of the acoustic matching section 16 needs to be an acoustic impedance that is intermediate between the acoustic impedance of the test subject 5 and the acoustic impedance of PZT. Beryllium is not suitable because the condition for acoustic impedance is not satisfied by metal when the test subject 5 is a human body.

When k1=1 and k2=5, then Cs=2667 m/s. One available material corresponding to this Cs is a polymer material. A polymer material is indicative of, for example, a synthetic fiber, synthetic resin, or synthetic rubber. Polymer materials have a high acoustic impedance and satisfy the condition for acoustic impedance when the first piezoelectric bodies 14 and the second piezoelectric bodies 15 are bulk-type, and can therefore be used. When the first piezoelectric bodies 14 and the second piezoelectric bodies 15 are thin-film-type, then the condition for acoustic impedance is not satisfied, and therefore polymer materials cannot be used.

When k1=1 and k2=7, then Cs=1600 m/s. One available material corresponding to this Cs is a natural rubber. A natural rubber satisfies the condition for acoustic impedance and also has favorable workability, and can therefore be used.

When k1=1 and k2=9, then Cs=1143 m/s. One available material corresponding to this Cs is a silicone resin. A silicone resin satisfies the condition for acoustic impedance and also has favorable workability, and therefore can be used as the material for the acoustic matching section 16.

When k1=3 and k2=7, then Cs=8000 m/s. Materials corresponding to this Cs are limited to special metals such as beryllium. Beryllium is not suitable because the condition for acoustic impedance is not satisfied by metal when the test subject 5 is a human body. When k1=3 and k2=9, then Cs=2667 m/s. One available material corresponding to this Cs is a polymer material.

FIG. 5 is a drawing illustrating the result of material selection for when the order n of harmonic imaging=3. As illustrated in FIG. 5, PZT is selected for the material for the first piezoelectric bodies 14 and the second piezoelectric bodies 15, and n=3 is selected. When k1=1 and k2=5, then Cs=8000 m/s. Materials corresponding to this Cs are limited to special metals such as beryllium. The special metals are not suitable because the condition for acoustic impedance is not satisfied.

When k1=1 and k2=7, then Cs=4000 m/s. One available material corresponding to this Cs is ceramics. Ceramics have a high acoustic impedance and satisfy the condition for acoustic impedance when the first piezoelectric bodies 14 and the second piezoelectric bodies 15 are bulk-type, and can therefore be used. When the first piezoelectric bodies 14 and the second piezoelectric bodies 15 are thin-film-type, then the condition for acoustic impedance is not satisfied, and therefore ceramics cannot be used. Ceramics necessitate a step for polishing in order to adjust the thickness after sintering, and are therefore not suitable in terms of workability.

When k1=1 and k2=9, then Cs=2667 m/s. One available material corresponding to this Cs is a polymer material. When k1=1 and k2=11, then Cs=2000 m/s. One available material corresponding to this Cs is a polyethylene resin. A polyethylene resin satisfies the condition for acoustic impedance and also has favorable workability, and can therefore be used.

When k1=3 and k2=11, then Cs=8000 m/s. Materials corresponding to this Cs are limited to special metals such as beryllium. The special metals are not suitable because the condition for acoustic impedance is not satisfied. When k1=3 and k2=13, then Cs=4000 m/s. One available material corresponding to this Cs is ceramics. When k1=3 and k2=15, then Cs=2667 m/s. One available material corresponding to this Cs is a polymer material.

When n=2, then natural rubbers and silicone resins can be favorably used for the acoustic matching section 16. When n=3, then polyethylene resins can be favorably used for the acoustic matching section 16. At this time, the acoustic waves 21 can be efficiently passed through the acoustic matching section 16 even though the first surface 13*a* and the second surface 16*a* have been flattened.

Figure 6:
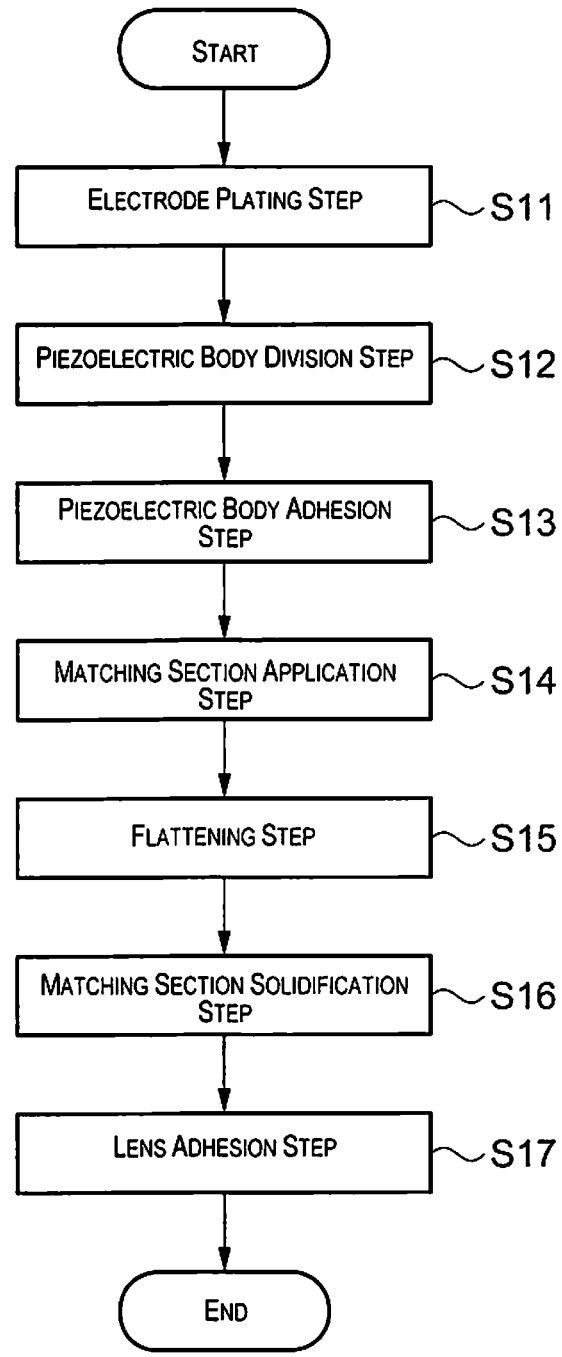
FIG. 6 is a flowchart illustrating a method of manufacturing an ultrasonic sensor.
Figure 7:
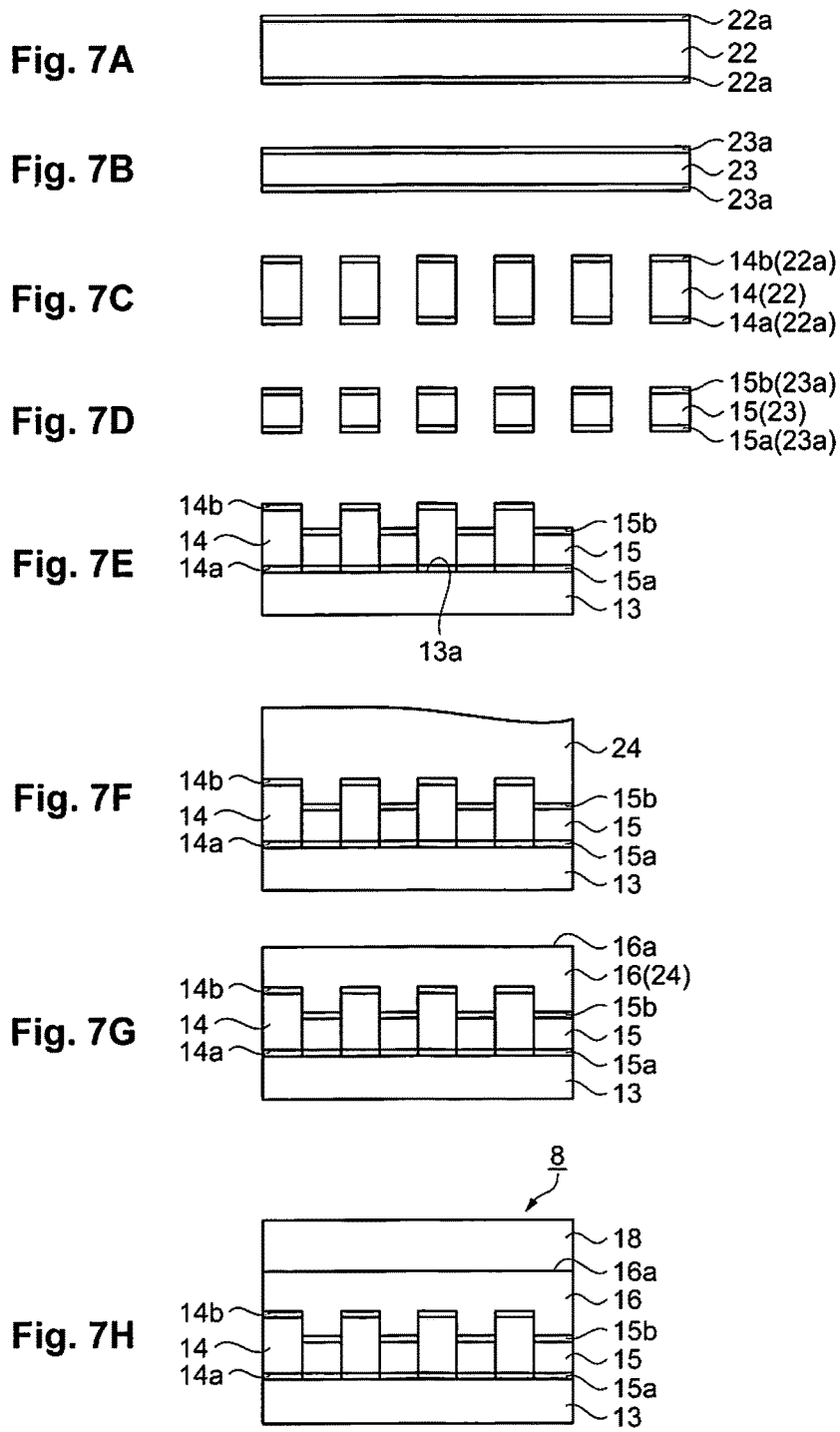
FIGS. 7A to 7H are schematic diagrams for describing a method of manufacturing an ultrasonic sensor.

Next, a method of manufacturing the ultrasonic sensor 8 described above shall be described, with reference to FIGS. 6 and 7A to 7H. FIG. 6 is a flowchart of the method of manufacturing the ultrasonic sensor, and FIGS. 7A to 7H are schematic diagrams for describing the method of manufacturing the ultrasonic sensor. In the flowchart in FIG. 6, the step S11 corresponds to an electrode plating step. This is a step where the first electrodes 14*a* and the second electrodes 14*b* are formed of the material for the first piezoelectric bodies 14, and the first electrodes 15*a* and the second electrodes 15*b* are formed of the material for the second piezoelectric bodies 15. Next is a transition to a step S12. The step S12 corresponds to a piezoelectric body division step. This step is a step where rod-shaped piezoelectric bodies are divided and the first piezoelectric bodies 14 and the second piezoelectric bodies 15 are formed. Next is a transition to a step S13.

The step S13 corresponds to a piezoelectric body adhesion step. This step is a step where the first piezoelectric bodies 14 and the second piezoelectric bodies 15 are adhered to the substrate 13. Next is a transition to a step S14. The step S14 corresponds to a matching section application step. This step is a step where the material for the acoustic matching section 16 is applied. Next is a transition to a step S15. The step S15 corresponds to a flattening step. This step is a step where the upper surface of the applied material for the acoustic matching section 16 is flattened. Next is a transition to a step S16. The step S16 corresponds to a matching section solidification step. This step is a step where the material for the acoustic matching section 16 is solidified. Next is a transition to a step S17. The step S17 corresponds to a lens adhesion step. This is a step where the acoustic lens 18 is adhered to the acoustic matching section 16. The steps above complete the ultrasonic sensor 8.

Next, the method of manufacture shall be described in greater detail, with reference to FIGS. 7A to 7H and in correspondence with steps illustrated in FIG. 6. FIGS. 7A and 7B are drawings corresponding to the electrode plate step in step S11. As illustrated in FIGS. 7A and 7B, a first piezoelectric body plate 22 and a second piezoelectric body plate 23 are prepared in the step S11. The first piezoelectric body plate 22 is the material for the first piezoelectric bodies 14, and the second piezoelectric body plate 23 is the material for the second piezoelectric bodies 15.

Metal films 22*a* are formed on opposing surfaces of the first piezoelectric body plate 22. Electroless plating or sputtering can be used as a method of forming the metal films 22*a*. The metal films 22*a* may also be thickened with electroplating. Likewise, metal films 23*a* are formed on opposing surfaces of the second piezoelectric body plate 23. A method similar to the method of forming the metal films 22*a* can be used as a method of forming the metal films 23*a*.

FIGS. 7C and 7D are drawings corresponding to the piezoelectric body division step in the step 12. As illustrated in FIG. 7C, the first piezoelectric body plate 22 is cut into rods in the step S12. A dicing device or wire saw cutting machine can be used in a method of cutting the first piezoelectric body plate 22. The first piezoelectric body plate 22 is cut and one of the metal films 22*a* becomes the first electrodes 14*a* while the other becomes the second electrodes 14*b*. Likewise, as illustrated in FIG. 7D, the second piezoelectric body plate 23 is cut into rods. A device similar to the device that cuts the first piezoelectric body plate 22 can be used for a device for cutting the second piezoelectric body plate 23. The second piezoelectric body plate 23 is cut and one of the metal films 23*a* becomes the first electrodes 15*a* while the other becomes the second electrodes 15*b*.

FIG. 7E is a drawing corresponding to the piezoelectric body adhesion step in the step S13. As illustrated in FIG. 7E, the first piezoelectric bodies 14 and the second piezoelectric bodies 15 are arrayed and adhered onto the substrate 13 in the step S13. The first piezoelectric bodies 14 and the second piezoelectric bodies 15 are arranged alternately side by side with one another. At this time, the first surface 13a of the substrate 13 is a flat surface, and therefore the first surface 13a is a surface that is easy to form. Then, because the first surface 13a of the substrate 13 is a flat surface, the first piezoelectric bodies 14 and the second piezoelectric bodies 15 can be easily arranged thereon.

FIG. 7F is a drawing corresponding to the matching section application step in the step S14. As illustrated in FIG. 7F, an acoustic matching section material 24 is applied by being overlaid onto the first piezoelectric bodies 14 and the second piezoelectric bodies 15 in the step S14. The acoustic matching section material 24 is what is obtained when a solvent is added to the material that was set in the step S5. The solvent is added to the acoustic matching section material 24 so as to facilitate the application, and the viscosity of the acoustic matching section material 24 is adjusted.

FIG. 7G is a drawing corresponding to the flattening step in the step S15 and the matching section solidification step in the step S16. As illustrated in FIG. 7G, the upper surface of the acoustic matching section material 24 is flattened in the step S15. The acoustic matching section material 24 is a liquid that is viscous to an appropriate degree. A method of scraping the upper surface of the applied acoustic matching section material 24 with a straight plate can be used as a method of flattening. The plate with which the scraping is done is called a squeegee.

Next, the acoustic matching section material 24 is dried and the solvent that is included in the acoustic matching section material 24 is evaporated in the step S16. To dry the acoustic matching section material 24, using a temperature-adjustable thermostatic chamber makes it possible to dry with excellent quality. The temperature and duration of drying are set in accordance with the material for the acoustic matching section material 24. As a result, the acoustic matching section material 24 solidifies and becomes the acoustic matching section 16. The second surface 16a of the acoustic matching section 16 becomes a flat surface.

FIG. 7H is a drawing corresponding to the lens adhesion step in the step S17. As illustrated in FIG. 7H, the acoustic lens 18 is adhered to the acoustic matching section 16 in the step S17. Because the second surface 16a of the acoustic matching section 16 has been made into a flat surface, the acoustic matching section 16 and the acoustic lens 18 can be easily adhered to one another such that a spacing does not form between the acoustic matching section 16 and the acoustic lens 18. The adhesive material is selected in accordance with the acoustic matching section 16. The steps above complete the ultrasonic sensor 8.

As described above, according to the present embodiment, the following effects are present.

(1) According to the present embodiment, the first surface 13a of the substrate 13 is a flat surface. As such, the shape facilitates processing compared to when unevenness is provided to the first surface 13a of the substrate 13. Moreover, the second surface 16a of the acoustic matching section 16 is also a flat surface. As such, the acoustic matching section 16 has a shape that facilitates processing compared to when unevenness is provided to the second surface 16a. As a result, the ultrasonic device 17 can be manufactured at high productivity.

(2) According to the present embodiment, as illustrated with the formula (4), f2, which is the resonant frequency of the second piezoelectric bodies 15, is an integer multiple of f1, which is the resonant frequency of the first piezoelectric bodies 14. As such, the first piezoelectric bodies 14 output ultrasonic waves, and the second piezoelectric bodies 15 can detect the n-th order high frequency of the reflected waves 21a that are reflected in the test subject 5. Having the thickness d1 of the first piezoelectric bodies be as illustrated by the formula (2) makes it possible to have the resonant frequency of the first piezoelectric bodies 14 be f1. Likewise, having the thickness d2 of the second piezoelectric bodies 15 be as illustrated by the formula (3) makes it possible to have the resonant frequency of the second piezoelectric bodies be f2.

(3) According to the present embodiment, there is a relationship $\lambda=Cs/f$, where $\lambda$ is the wavelength of the ultrasonic waves 21 traveling through the acoustic matching section 16 and f is the frequency. Then, the formula (8) illustrates $t1=k1>\lambda/4$, and the formula (11) illustrates $t2=k2\times\lambda/4$. In other words, the ultrasonic waves 21 traveling through the acoustic matching section 16 are an odd multiple of $\lambda/4$. This curbs any incidence where the ultrasonic waves 21 traveling through the acoustic matching section 16 would cancel each other out with the ultrasonic waves 21 reflected in the interface of the acoustic matching section 16. As such, the acoustic matching section 16 can allow the ultrasonic waves 21 to travel through efficiently.

(4) According to the present embodiment, as illustrated by the formula (1), the thickness obtained by adding the first piezoelectric body thickness 14c and the first acoustic matching section thickness 16d will be the same thickness as the thickness obtained by adding the second piezoelectric body thickness 15c and the second acoustic matching section thickness 16e. By so doing, when the first surface 13a on which the first piezoelectric bodies 14 and the second piezoelectric bodies 15 are installed in the substrate 13 is flat, then the second surface 16a of the acoustic matching section 16 will also be flat. Then, Cs is computed by setting n, k1, k2, and Cp as illustrated in the formula (14). Having the material of the acoustic matching section 16 be a material that corresponds to the computed Cs makes it possible to manufacture at high productivity an ultrasonic device 17 with which the ultrasonic waves 21 travel efficiently through the acoustic matching section 16.

(5) According to the present embodiment, Cs will=1600 m/s when n=2, k1=1, k2=7, and Cp=4000 m/s in the formula (14). Then, a natural rubber fits for when Cs=1600 m/s. Natural rubbers have excellent workability. As such, using a natural rubber for the material of the acoustic matching section 16 makes it possible to manufacture at high productivity an ultrasonic device 17 with which the ultrasonic waves 21 travel efficiently through the acoustic matching section 16.

(6) According to the present embodiment, Cs will=1143 m/s when n=2, k1=1, k2=9, and Cp=4000 m/s in the formula (14). Then, a silicone resin fits for when Cs=1143 m/s. Silicone resins have excellent workability. As such, using a silicone resin for the material of the acoustic matching section 16 makes it possible to manufacture at high productivity an ultrasonic device 17 with which the ultrasonic waves 21 travel efficiently through the acoustic matching section 16.

(7) According to the present embodiment, Cs will=2000 m/s when n=3, k1=1, k2=11, and Cp=4000 m/s in the formula (14). Then, a polyethylene resin fits for when Cs=2000 m/s. Polyethylene resins have excellent workability. As such, using a polyethylene resin for the material of the acoustic matching section 16 makes it possible to manufacture at high productivity an ultrasonic device 17 with which the ultrasonic waves 21 travel efficiently through the acoustic matching section 16.

(8) According to the present embodiment, the first surface 13a of the substrate 13 is a flat surface. As such, the first surface 13a is easier to form compared to when there is unevenness. Then, the first piezoelectric bodies 14 and the second piezoelectric bodies 15 are installed onto the first surface 13a. The first piezoelectric bodies 14 and the second piezoelectric bodies 15 can be installed easily because the first surface 13a is a flat surface. The second surface 16a of the acoustic matching section 16 is a flat surface. As such, the second surface 16a and the acoustic lens 18 can be easily adhered to one another such that a spacing does not form between the second surface 16a and the acoustic lens 18.

Second Embodiment

Figure 8:
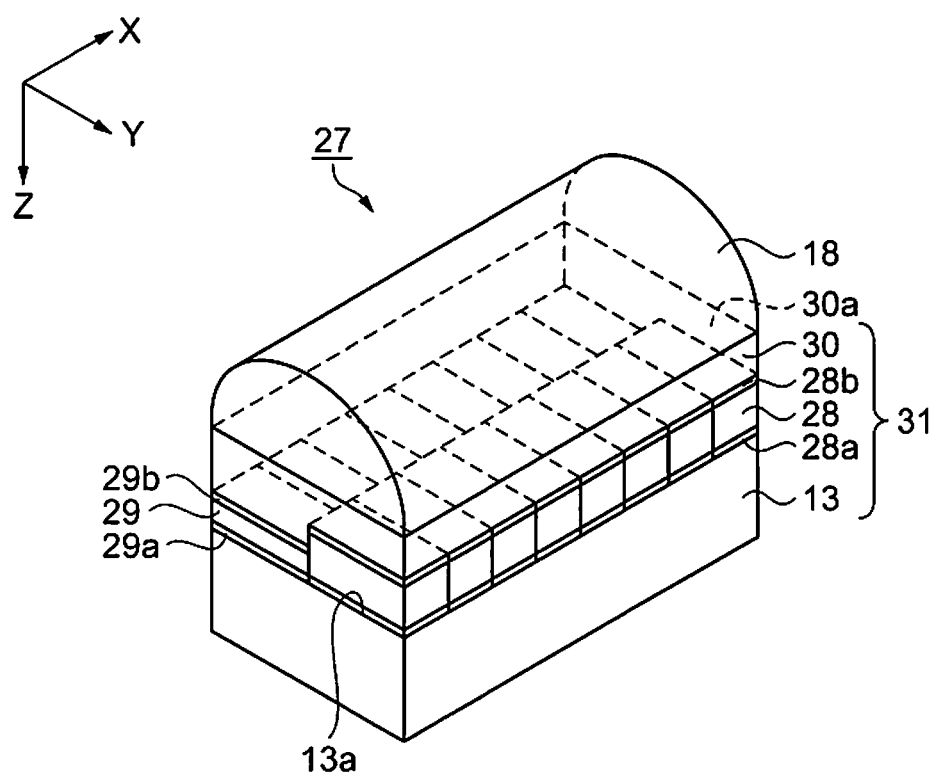
FIG. 8 is a schematic perspective view illustrating a structure of an ultrasonic sensor as in a second embodiment.

Next, as regards one embodiment of an ultrasonic sensor having a characteristic structure, FIG. 8 is a schematic perspective view illustrating the structure of an ultrasonic sensor. The present embodiment differs from the first embodiment in the arrangement of the first piezoelectric bodies 14 and the second piezoelectric bodies 15 illustrated in FIG. 1B. Matters where the present embodiment is the same as the first embodiment are omitted from the description here.

Namely, in the present embodiment, as illustrated in FIG. 8, an ultrasonic sensor 27 is provided with the substrate 13, and first piezoelectric bodies 28 and second piezoelectric bodies 29 are arranged on the first surface 13a. Because the first surface 13a is a flat surface, the first piezoelectric bodies 28 and the second piezoelectric bodies 29 are easily arranged on the first surface 13a. The shape of the first piezoelectric bodies 28 is a prism, and first electrodes 28a are installed on a surface of the first piezoelectric bodies 28 facing the substrate 13 side. Second electrodes 28b are installed on a surface of the opposite side to the first electrodes 28a in the first piezoelectric bodies 28.

The shape of the second piezoelectric bodies 29 is also a prism, and the length of the second piezoelectric bodies 29 in the Y-direction is the same length as that of the first piezoelectric bodies 28. The length of the X-direction width of the second piezoelectric bodies 29 is also the same length as that of the first piezoelectric bodies 28. The length of the Z-direction thickness of the second piezoelectric bodies 29 is a shorter length than that of the first piezoelectric bodies 28. First electrodes 29a are installed on a surface of the second piezoelectric bodies 29 facing the substrate 13 side. Second electrodes 29b are installed on a surface of the opposite side to the first electrodes 29a in the second piezoelectric bodies 29.

The first piezoelectric bodies 28 are arranged on the Y-direction side on the first surface 13a, and the second piezoelectric bodies 29 are arranged on the −Y-direction side. The first piezoelectric bodies 28 and the second piezoelectric bodies 29 are arrayed side by side in the X-direction.

For the sake of simplifying the drawings, the depicted first piezoelectric bodies 28 and second piezoelectric bodies 29 are arranged each in increments of eight. The numbers of first piezoelectric bodies 28 and second piezoelectric bodies 29 are not particularly limited. When the numbers are greater, the examination range can be widened by a commensurate amount. Alternatively, the resolution can be increased. In the present embodiment, for example, there are 256 of the first piezoelectric bodies 28 and the second piezoelectric bodies 29, each.

An acoustic matching section 30 is installed on the −Z-side of the first piezoelectric bodies 28 and the second piezoelectric bodies 29. The material of the acoustic matching section 30 is the same material as that of the acoustic matching section 16 in the first embodiment. The substrate 13, the first piezoelectric bodies 28, the second piezoelectric bodies 29, the acoustic matching section 30, and the like constitute an ultrasonic device 31. The acoustic lens 18 is installed on the acoustic matching section 30. A second surface 30a, which is a surface of the acoustic matching section 30 that faces the acoustic lens 18, is a flat surface. As such, the second surface 30a and the acoustic lens 18 can be easily adhered to one another such that a spacing does not form between the acoustic matching section 30 and the acoustic lens 18.

The thickness of the first piezoelectric bodies 28 is the same thickness as that of the first piezoelectric body thickness 14c of the first piezoelectric bodies 14 in the first embodiment. The material of the first piezoelectric bodies 28 is the same material as that of the first piezoelectric bodies 14. Likewise, the thickness of the second piezoelectric bodies 29 is also the same thickness as that of the second piezoelectric body thickness 15c of the second piezoelectric bodies 15 in the first embodiment. The material of the second piezoelectric bodies 29 is the same material as that of the second piezoelectric bodies 15.

The material of the acoustic matching section 30 is the same material as that of the acoustic matching section 16 in the first embodiment. In the acoustic matching section 30, the thickness of the location that faces the first piezoelectric bodies 28 is the same thickness as that of the first acoustic matching section thickness 16d, and the thickness of the location that faces the second piezoelectric bodies 29 is the same thickness as that of the second acoustic matching section thickness 16e.

As such, the ultrasonic sensor 27 can emit the ultrasonic waves 21 efficiently. It then becomes possible to efficiently detect the higher-order reflected waves 21a that are reflected by the test subject 5.

Third Embodiment

Next, an embodiment of manufacturing an ultrasonic sensor shall be described, with reference to FIGS. 9 and 10. The present embodiment differs from the first embodiment in that the first piezoelectric bodies 14 and the second piezoelectric bodies 15 are changed from bulk-type to thin-film-type. Matters where the present embodiment is the same as the first embodiment are omitted from the description here.

Figure 9A:
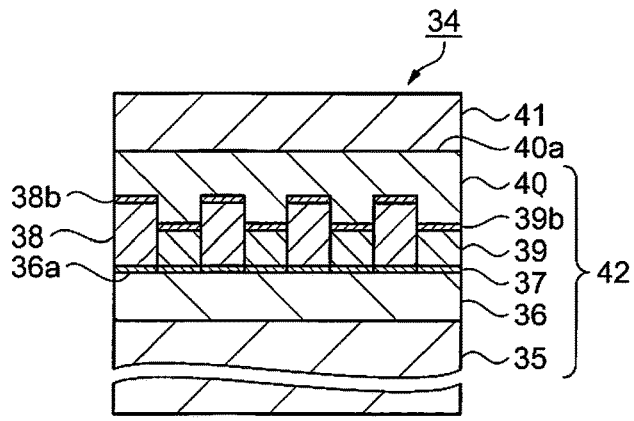
FIG. 9A is a schematic lateral cross-sectional view illustrating a structure of an ultrasonic sensor and FIG. 9B is a flowchart illustrating a method of manufacturing an ultrasonic sensor according to a third embodiment.

FIG. 9A is a schematic lateral cross-sectional view illustrating a structure of an ultrasonic sensor. As illustrated in FIG. 9A, an ultrasonic sensor 34 is provided with a backing substrate 35. The backing substrate 35 is a site corresponding to the substrate 13 of the first embodiment. A substrate 36 is installed onto the backing substrate 35. The substrate 36 is not particularly limited, provided that the substrate be one with heat resistance, such as a silicon substrate or a glass substrate. In the present embodiment, for example, a silicon substrate is used for the substrate 36.

In the substrate 36, first electrodes are installed on an opposite side of the backing substrate 35. Between the substrate 36 and the first electrodes 37, there is an insulating film (not shown) that is formed. The insulating film could be, for example, a film of silicon dioxide or silicon nitride. The materials for the first electrodes 37 are layers of iridium, iridium oxide, and platinum stacked in the stated order from the substrate 36 side. Iridium, iridium oxide, and platinum are endowed with functions as an orientation control, a reducing gas barrier, and a seed layer, respectively.

Onto the first electrodes 37 are first piezoelectric bodies 38 and second piezoelectric bodies 39 arranged, in alternation. The first piezoelectric bodies 38 and the second piezoelectric bodies 39 are constituted of PZT. Second electrodes 38b are installed on the first piezoelectric bodies 38, and second electrodes 39b are installed on the second piezoelectric bodies 39. An acoustic matching section 40 is installed onto the second electrodes 38b and second electrodes 39b. An acoustic lens 41 is furthermore installed onto the acoustic matching section 40. The materials for the second electrodes 38b and the second electrodes 39b are layers of platinum, iridium oxide, and iridium stacked in the stated order from the first piezoelectric body 38 and second piezoelectric body 39 side.

The first piezoelectric bodies 38, the second piezoelectric bodies 39, the acoustic matching section 40, and the acoustic lens 41 are sites corresponding to the first piezoelectric bodies 14, the second piezoelectric bodies 15, the acoustic matching section 16, and the acoustic lens 18, respectively, in the first embodiment. The thicknesses of the first piezoelectric bodies 38, the second piezoelectric bodies 39, and the acoustic matching section 40 are set in accordance with the formulae (1) to (14). As such, it becomes possible to efficiently emit the ultrasonic waves 21 and to efficiently detect the reflected waves 21a.

A first surface 36a, which is the surface of the substrate 36 on which the first electrodes 37 are installed, is a flat surface, making the surface easy to process. A second surface 40a, which is a surface that faces the acoustic lens 41 in the acoustic matching section 40, is also a flat surface, making the surface easy to process. Because the second surface 40a is flat, it becomes possible to easily bond the acoustic matching section 40 and the acoustic lens 41 together such that a spacing is not formed between the acoustic matching section 40 and the acoustic lens 41. The configuration from the backing substrate 35 to the acoustic matching section 40 is an ultrasonic device 42.

Figure 9B:
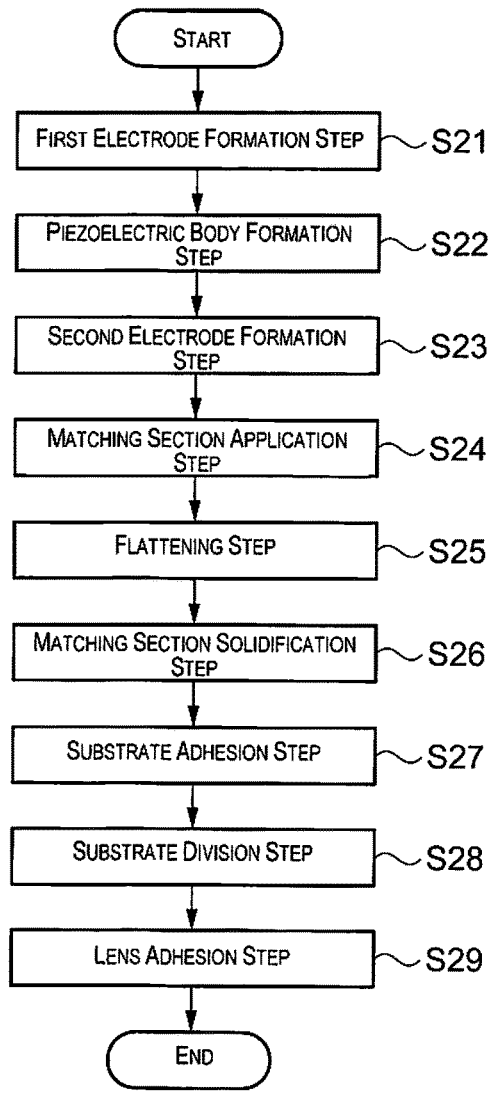

Next, a method of manufacturing the ultrasonic sensor 34 described above shall be described with reference to FIGS. 9B and 10A to 10F. FIG. 9B is a flowchart for a method of manufacturing an ultrasonic sensor, and FIGS. 10A to 10F are schematic diagrams for describing a method of manufacturing an ultrasonic sensor. In the flowchart in FIG. 9B, a step S21 corresponds to a first electrode formation step. This is a step where the insulating film and the first electrodes 37 are formed on the first surface 36a of the substrate 36. Next is a transition to a step S22. The step S22 corresponds to a piezoelectric body formation step. This step is a step where the first piezoelectric bodies 38 and the second piezoelectric bodies 39 are formed on the first electrodes 37. Next is a transition to a step S23.

The step S23 corresponds to a second electrode formation step. This step is a step where the second electrodes 38b are formed on the first piezoelectric bodies 38 and the second electrodes 39b are formed on the second piezoelectric bodies 39. Next is a transition to a step S24. The step S24 corresponds to a matching section application step. This step is a step where the material for the acoustic matching section 40 is applied. Next is a transition to a step S25. The step S25 corresponds to a flattening step. This step is a step where the upper surface of the applied material for the acoustic matching section 40 is flattened. Next is a transition to a step S26. The step S26 corresponds to a matching section solidification step. This step is a step where the material for the acoustic matching section 40 is solidified. Next is a transition to a step S27. The step S27 corresponds to a substrate adhesion step. This step is a step where the substrate 36 is adhered to the backing substrate 35. Next is a transition to a step S28. The step S28 corresponds to a substrate division step. This step is a step where the backing substrate 35 and the substrate 36 are divided. Next is a transition to a step S29. The step S29 corresponds to a lens adhesion step. This is a step where the acoustic lens 41 is adhered to the acoustic matching section 40. The steps above complete the ultrasonic sensor 34.

Figure 10A:
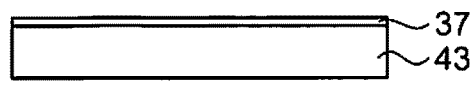

Next, the method of manufacture shall be described in greater detail, with reference to FIGS. 10A to 10F and in correspondence with steps illustrated in FIG. 9B. FIG. 10A is a drawing corresponding to the first electrode formation step in the step S21. As illustrated in FIG. 10A, in the step S21, first, a mother substrate 43 is prepared. The mother substrate 43 is large enough to allow for a plurality of the substrates 36 to be arranged. The mother substrate 43 is oxidized to form an oxide film. The oxide film functions as the insulating film. Next, a solid film composed of the materials for the first electrodes 37 is formed on the mother substrate 43. Sputtering can be used for the solid film. Next, photolithography is used to pattern the solid film and form the first electrodes 37.

Figure 10B:
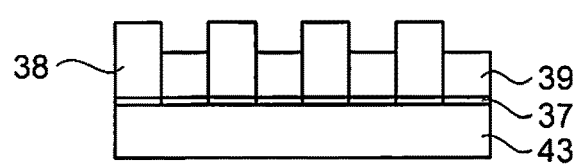

FIG. 10B is a drawing corresponding to the piezoelectric body formation step in the step S22. As illustrated in FIG. 10B, the first piezoelectric bodies 38 and the second piezoelectric bodies 39 are formed on the first electrodes 37. The first piezoelectric bodies 38 and the second piezoelectric bodies 39 are formed, for example, by repeatedly performing film formation using sputtering or a sol-gel method and then patterning.

Figure 10C:
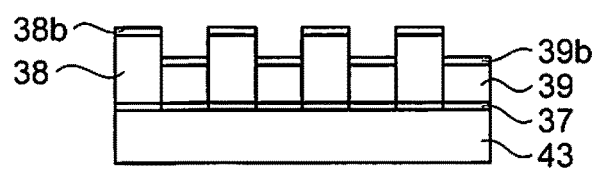

FIG. 10C is a drawing corresponding to the second electrode formation step in the step S23. As illustrated in FIG. 10C, the second electrodes 38b are formed on the first piezoelectric bodies 38, and the second electrodes 39b are formed on the second piezoelectric bodies 39. The second electrodes 38b and the second electrodes 39b are formed using photolithography on a solid film formed by sputtering.

Figure 10D:
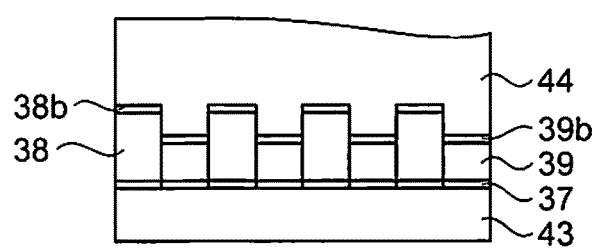

FIG. 10D is a drawing corresponding to the matching section application step in the step S24. As illustrated in FIG. 10D, the acoustic matching section material 44 is applied overlaid onto the first piezoelectric bodies 38 and second piezoelectric bodies 39 in the step S24. The acoustic matching section material 44 is what is obtained when a solvent is added to the material that was set in the step S5. The solvent is added to the acoustic matching section material 44 so as to facilitate the application, and the viscosity of the acoustic matching section material 44 is adjusted.

Figure 10E:
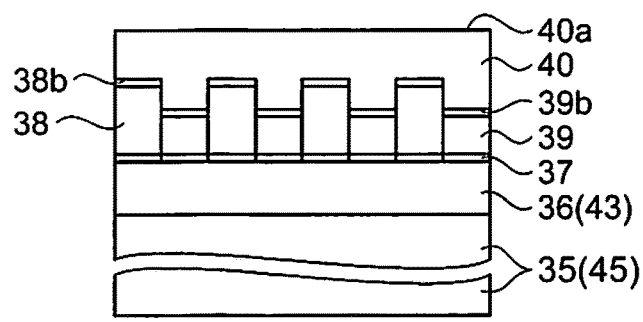

FIG. 10E is a drawing corresponding to the flattening step in the step S25, the matching section solidification step in the step S26, the substrate adhesion step in the step S27, and the substrate division step in the step S28. As illustrated in FIG. 10E, the upper surface of the acoustic matching section material 44 is flattened in the step S25. The acoustic matching section material 44 is a liquid that is viscous to an appropriate degree. A method of scraping the upper surface of the applied acoustic matching section material 24 with a straight plate can be used as a method of flattening.

Next, the acoustic matching section material 44 is dried and the solvent that is included in the acoustic matching section material 44 is evaporated in the step S26. To dry the acoustic matching section material 44, using a temperature-adjustable thermostatic chamber makes it possible to dry with excellent quality. The temperature and duration of drying are set in accordance with the material for the acoustic matching section material 44. As a result, the acoustic matching section material 44 solidifies and becomes the acoustic matching section 40. The second surface 40a of the acoustic matching section 40 is a flat surface.

Next, in the step S27, a large backing substrate 45 is prepared. The large backing substrate 45 is large enough that a plurality of backing substrates 35 can be arranged thereon. Then, the large backing substrate 45 and the mother substrate 43 are adhered together. Then, in the step S28, the large backing substrate 45 and the mother substrate 43 are divided with a dicer. The mother substrate 43 is divided and becomes the substrates 36, and the large backing substrate 45 is divided and becomes the backing substrates 35. The backing substrates 35 and the substrates 36 are the size of the ultrasonic sensor 34.

Figure 10F:
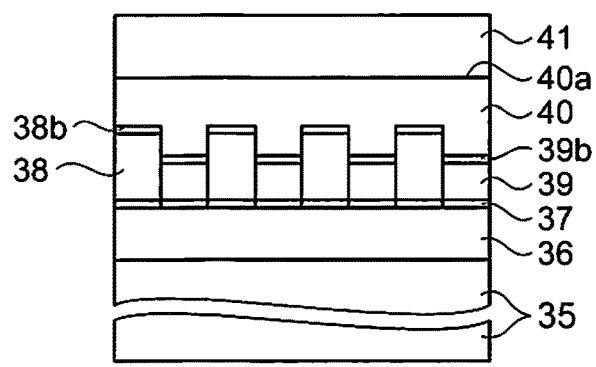

FIG. 10F is a drawing corresponding to the lens adhesion step in the step S29. As illustrated in FIG. 10F, the acoustic lens 41 is adhered to the acoustic matching section 40 in the step S29. Because the second surface 40a of the acoustic matching section 40 is flat, it becomes possible to easily bond the acoustic matching section 40 and the acoustic lens 41 together such that a spacing is not formed between the acoustic matching section 40 and the acoustic lens 41. The adhesive material is selected in accordance with the acoustic matching section 40. The steps above complete the ultrasonic sensor 34.

As described above, according to the present embodiment, the following effects are present.

(1) According to the present embodiment, the first piezoelectric bodies 38 and the second piezoelectric bodies 39 are formed using photolithography. As such, a large number of the first piezoelectric bodies 38 and the second piezoelectric bodies 39 can be formed on a narrow surface area. As such, the ultrasonic sensor 34 can be made into a high-resolution sensor.

The present invention is in no way limited to the embodiments described above, and it would also be possible for a variety of modifications or improvements to be added by a person having ordinary skill in the art without departing from the teachings of the present invention. Modification examples shall be described below.

Modification Example 1

In the first embodiment, the ultrasonic sensor 8 was installed onto the ultrasonic probe 3 of the ultrasonic image apparatus 1. The ultrasonic sensor 27 of the second embodiment may also be installed onto the ultrasonic probe 3. The ultrasonic sensor 34 of the third embodiment may be installed onto the ultrasonic probe 3. At this time, the ultrasonic sensors 27, 34 would still be able to efficiently emit the ultrasonic waves 21 and efficiently receive the reflected waves 21a.

Modification Example 2

In the first embodiment, acoustic matching sections 16 for a case where the order n of harmonic imaging=2 and a case where n=3 were selected. n may also be 4 or higher. A higher order for n means that the resolution at which the reflected waves 21a are detected can be raised.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic device comprising:
   a substrate having a first surface, the first surface being a flat surface;
   a first piezoelectric body disposed on the first surface of the substrate;
   a second piezoelectric body disposed on the first surface of the substrate, the second piezoelectric body having a different thickness from a thickness of the first piezoelectric body as measured from the first surface of the substrate; and
   an acoustic matching section disposed on the first piezoelectric body and the second piezoelectric body, the acoustic matching section having a first side facing the first piezoelectric body and the second piezoelectric body, and a second side opposite from the first side, a surface of the acoustic matching section on the second side being a flat surface parallel with the first surface of the substrate, wherein $$f2 = n \times f1 \qquad \text{formula (1)}$$

$$d1 = Cp/(2 \times f1) \qquad \text{formula (2)}$$

$$d2 = Cp/(2 \times f2) \qquad \text{formula (3)}$$

$$t1 = k1 \times Cs/(4 \times f1) \qquad \text{formula (4)}$$

$$t2 = k2 \times Cs/(4 \times f2) \qquad \text{formula (5)}$$

$$d1 + t1 = d2 + t2 \qquad \text{formula (6)}$$

$$Cs = 2 \times (n-1) \times Cp(k2 - n \times k1) \qquad \text{formula (7),}$$

wherein formulae (1) to (7) are satisfied, where Cp is a speed of sound in the first piezoelectric body and the second piezoelectric body, Cs is a speed of sound in the acoustic matching section, f1 is a resonant frequency of the first piezoelectric body, f2 is a resonant frequency of the second piezoelectric body, d1 is the thickness of the first piezoelectric body, d2 is the thickness of the second piezoelectric body, t1 is a thickness of the acoustic matching section as measured from a surface of the first piezoelectric body, t2 is a thickness of the acoustic matching section as measured from a surface of the second piezoelectric body, n is an integer 2 or higher, and k1 and k2 are odd numbers.

2. The ultrasonic device according to claim 1, wherein the acoustic matching section is made of natural rubber.

3. The ultrasonic device according to claim 1, wherein the acoustic matching section is made of silicone resin.

4. The ultrasonic device according to claim 1, wherein the acoustic matching section is made of polyethylene resin.

5. An ultrasonic probe comprising:
the ultrasonic device according to claim 1; and
a drive section configured and arranged to drive the ultrasonic device.

6. An ultrasonic diagnostic apparatus comprising:
the ultrasonic device according to claim 1, and configured and arranged to emit ultrasonic waves at a test subject and to detect ultrasonic waves that are reflected in the test subject;
a drive section configured and arranged to drive the ultrasonic device;
a reflection distribution computation section configured to compute distribution of reflectance of ultrasonic waves in the test subject from the ultrasonic waves detected by the ultrasonic device; and
a display section configured and arranged to display an image based on the distribution of reflectance of ultrasonic waves in the test subject as computed by the reflection distribution computation section.

* * * * *